United States Patent
Feng et al.

(10) Patent No.: US 11,135,036 B2
(45) Date of Patent: Oct. 5, 2021

(54) COMPUTER-BASED METHOD FOR MEASURING POSITIONAL RELATIONSHIP BETWEEN TWO TEETH

(71) Applicant: Wuxi EA Medical Instruments Technologies Limited, Jiangsu (CN)

(72) Inventors: Yang Feng, Shanghai (CN); Xiaolin Liu, Shanghai (CN); Jing Wang, Shanghai (CN)

(73) Assignee: Wuxi EA Medical Instruments Technologies Limited, Jiangsu (CN)

( * ) Notice: Subject to any disclaimer, the term of this patent is extended or adjusted under 35 U.S.C. 154(b) by 0 days.

(21) Appl. No.: 16/771,823

(22) PCT Filed: Feb. 14, 2019

(86) PCT No.: PCT/CN2019/075076
§ 371 (c)(1),
(2) Date: Jun. 11, 2020

(87) PCT Pub. No.: WO2019/196555
PCT Pub. Date: Oct. 17, 2019

(65) Prior Publication Data
US 2021/0169611 A1      Jun. 10, 2021

(30) Foreign Application Priority Data
Apr. 10, 2018   (CN) .......................... 201810319908.7

(51) Int. Cl.
*G06T 15/00*      (2011.01)
*A61C 7/00*       (2006.01)
(Continued)

(52) U.S. Cl.
CPC .............. *A61C 7/002* (2013.01); *A61C 19/05* (2013.01); *G06F 30/20* (2020.01); *G06T 7/0012* (2013.01);
(Continued)

(58) Field of Classification Search
CPC ......... G06T 15/00; A61C 13/00; A61C 11/00; A61C 19/05; A61C 19/045
(Continued)

(56) References Cited

U.S. PATENT DOCUMENTS

| 6,783,360 B2 * | 8/2004 | Chishti | ................... A61C 7/00 433/6 |
| 7,220,122 B2 * | 5/2007 | Chishti | ................... A61C 7/00 433/24 |

(Continued)

FOREIGN PATENT DOCUMENTS

| CN | 107260351 | 10/2017 |
| CN | 107374758 | 11/2017 |

(Continued)

OTHER PUBLICATIONS

Magne P, Gallucci GO, Belser UC. Anatomic crown width/length ratios of unworn and worn maxillary teeth in white subjects. The Journal of prosthetic dentistry. May 1, 2003;89(5):453-61.*

*Primary Examiner* — Phu K Nguyen
(74) *Attorney, Agent, or Firm* — Forge IP, PLLC (57) ABSTRACT

In one aspect, the present application provides a computer-based method of measuring positional relationship between two teeth, comprising: obtaining a second 3D digital model representing a plurality of teeth under a second tooth arrangement, wherein the plurality of teeth comprise a first tooth and a second tooth; and measuring a value of a collision or a size of a gap between the first tooth and second tooth based on the second 3D digital model and in a predetermined first direction.

8 Claims, 4 Drawing Sheets

(51) Int. Cl.
  *G06T 7/70*    (2017.01)
  *G16H 50/50*   (2018.01)
  *G06F 30/20*   (2020.01)
  *A61C 19/05*   (2006.01)
  *G06T 7/00*    (2017.01)
  *G06T 7/60*    (2017.01)
  *G06T 15/06*   (2011.01)
  *G06T 17/00*   (2006.01)
  *G06T 19/20*   (2011.01)

(52) U.S. Cl.
  CPC ............... *G06T 7/60* (2013.01); *G06T 7/70* (2017.01); *G06T 15/06* (2013.01); *G06T 17/00* (2013.01); *G06T 19/20* (2013.01); *G16H 50/50* (2018.01); *G06T 2207/30036* (2013.01); *G06T 2210/21* (2013.01); *G06T 2210/41* (2013.01); *G06T 2219/2008* (2013.01)

(58) Field of Classification Search
  USPC ........................................................ 345/418
  See application file for complete search history.

(56) References Cited

U.S. PATENT DOCUMENTS

| | | | |
|---|---|---|---|
| 7,695,278 B2 * | 4/2010 | Sporbert | A61C 9/0046 |
| | | | 433/24 |
| 8,469,705 B2 * | 6/2013 | Sachdeva | A61C 7/00 |
| | | | 433/24 |
| 9,572,636 B2 * | 2/2017 | Sporbert | G06T 19/003 |
| 9,782,236 B2 * | 10/2017 | Sporbert | G06F 30/00 |
| 10,722,325 B2 * | 7/2020 | Khakpour | A61C 1/082 |
| 2002/0150859 A1 | 10/2002 | Imgrund et al. | |

FOREIGN PATENT DOCUMENTS

| | | | |
|---|---|---|---|
| EP | 2 549 946 | * | 1/2013 |
| RU | 2286114 | | 10/2006 |
| WO | WO03092536 | | 11/2003 |

\* cited by examiner

COMPUTER-BASED METHOD FOR MEASURING POSITIONAL RELATIONSHIP BETWEEN TWO TEETH

FIELD OF THE APPLICATION

The present application generally relates to a computer-based method for measuring positional relationship between two teeth.

BACKGROUND

With the continuous development of computer science, dental professionals increasingly rely on computer techniques to improve the efficiency of dental diagnosis and treatment.

One of the applications is to analyze a three-dimensional (3D) digital model of teeth using a computer, to measure positional relationship between two teeth, for example, determining whether there is collision or a gap between the two teeth, and measure the depth of the collision or the size of the gap.

Currently, there are two commonly used methods of measuring the positional relationship between two teeth, both of which are based on a 3D digital model representing teeth under the current tooth arrangement.

In one method, first, K-tree data structures are constructed for the 3D digital models of the two teeth respectively, and then each node on the 3D digital models of the two teeth are traversed based on the data structures. If at least one node on the 3D digital model of one tooth is located within a closed surface of the 3D digital model of the other tooth, it is believed that there is collision between the two teeth, otherwise it is believed that there is a gap between the two teeth.

The other method is based on parting plane search, namely, searching for a parting plane between the 3D digital models of the two teeth. If at least one parting plane is found, it is believed that there is a gap between the two teeth, otherwise it is believed that there is a collision between the two teeth.

In a conventional method of measuring collision value (depth of collision) between two teeth, first, a first set of nodes which are on the 3D digital model of the first tooth and located in a closed surface formed by the 3D digital model of the second tooth, and a second set of nodes which are on the 3D digital model of the second tooth and located in a closed surface formed by the 3D digital model of the first tooth are identified, then each pair of nodes from the first set of nodes and the second set of nodes respectively are joined using a line segment, and the length of the longest line segment is taken as the collision value of the two teeth.

Similarly, in a conventional method of measuring a gap between two teeth, a distance between each pair of nodes of the two teeth respectively is calculated, and the minimum distance is taken as the gap size between the two teeth.

However, the Inventors of the present application discover that collision value and gap size obtained by conventional methods are of very limited value to clinical medicine.

SUMMARY

In one aspect, the present application provides a computer-based method of measuring positional relationship between two teeth, which comprises: obtaining a second 3D digital model representing a plurality of teeth under a second tooth arrangement, wherein the plurality of teeth comprise a first tooth and a second tooth; and measuring a collision value or a gap size between the first tooth and second tooth based on the second 3D digital model and a predetermined first direction.

In some embodiments, the first tooth and second tooth under the second tooth arrangement are at their target positions of orthodontic treatment.

In some embodiments, the computer-based method of measuring positional relationship between two teeth may further comprise: determining the first direction based on a second direction and a third direction, wherein the second direction is the mesiodistal direction of the first tooth when the plurality of teeth are under the second tooth arrangement, and the third direction is the mesiodistal direction of the second tooth when the plurality of teeth are under the second tooth arrangement.

In some embodiments, the computer-based method of measuring positional relationship between two teeth may further comprise: selecting a reference plane; projecting unit vectors representing the second direction and the third direction on the reference plane to obtain a first unit vector and a second unit vector; and calculating an average vector of the first unit vector and the second unit vector, wherein the direction of the average vector is taken as the first direction.

In some embodiments, the reference plane may be a functional occlusal plane.

In some embodiments, the reference plane may be a horizontal plane.

In some embodiments, the computer-based method of measuring positional relationship between two teeth may further comprise: obtaining a first 3D digital model representing the plurality of teeth under a first tooth arrangement, where the first tooth arrangement is different from the second tooth arrangement; and manipulating the first 3D digital model to obtain the second 3D digital model.

In some embodiments, the computer-based method of measuring positional relationship between two teeth may further comprise: generating a ray group along the first direction; and determining the collision value or the gap size between the first tooth and the second tooth based on intersection points of the ray group and the first and the second tooth.

In some embodiments, the computer-based method of measuring positional relationship between two teeth may further comprise: generating a vector set for each ray in the ray group using intersection points of the ray with the first tooth and the second tooth to obtain a vector set; and determining the collision value or the gap size between the first tooth and the second tooth based on the vector sets.

In some embodiments, the computer-based method of measuring positional relationship between two teeth may further comprise: projecting the first tooth and the second tooth on a first plane perpendicular to the first direction; and sampling in an overlap area of the projections of the first tooth and the second tooth to obtain a sampling point set based on which the ray group is generated.

BRIEF DESCRIPTION OF THE DRAWINGS

The above and other features of the present application will be further illustrated below with reference to figures and their detailed depictions. It should be appreciated that these figures only show several exemplary embodiments according to the present application, so they should not be construed as limiting the protection scope of the present application. Unless otherwise specified, the figures are not

DETAILED DESCRIPTION OF ILLUSTRATED EMBODIMENTS

In the following detailed description, reference is made to the accompanying drawings, which form a part thereof. Exemplary embodiments in the detailed description and figures are only intended for illustration purpose and not meant to be limiting. Inspired by the present application, those skilled in the art can understand that other embodiments may be utilized and other changes may be made, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

The Inventors of the present application discover that since conventional methods of measuring collision value or gap between teeth is based on a current tooth arrangement and have no control on the direction of the collision or gap, thus measured results are of very limited value to clinical medicine in many cases. For example, in orthodontic treatment, collision value or gap between two teeth measured using a conventional method is substantially of no value to clinical medicine when determining how much amount of which portion of which tooth shall be cut off to avoid interference between two teeth and when determining the shape and size of a denture to be mounted between two teeth.

After a lot of work, the Inventors of the present application discover that for a case which requires orthodontic treatment, when two teeth are at target positions, collision value or gap measured along a specific direction (which may be determined based on a specific treatment objective and/or specific conditions of a patient) is of greater value to diagnosis and therapy in clinical medicine.

An aspect of the present application provides a novel method of measuring relative positional relationship between two teeth using a computer.

Figure 1:
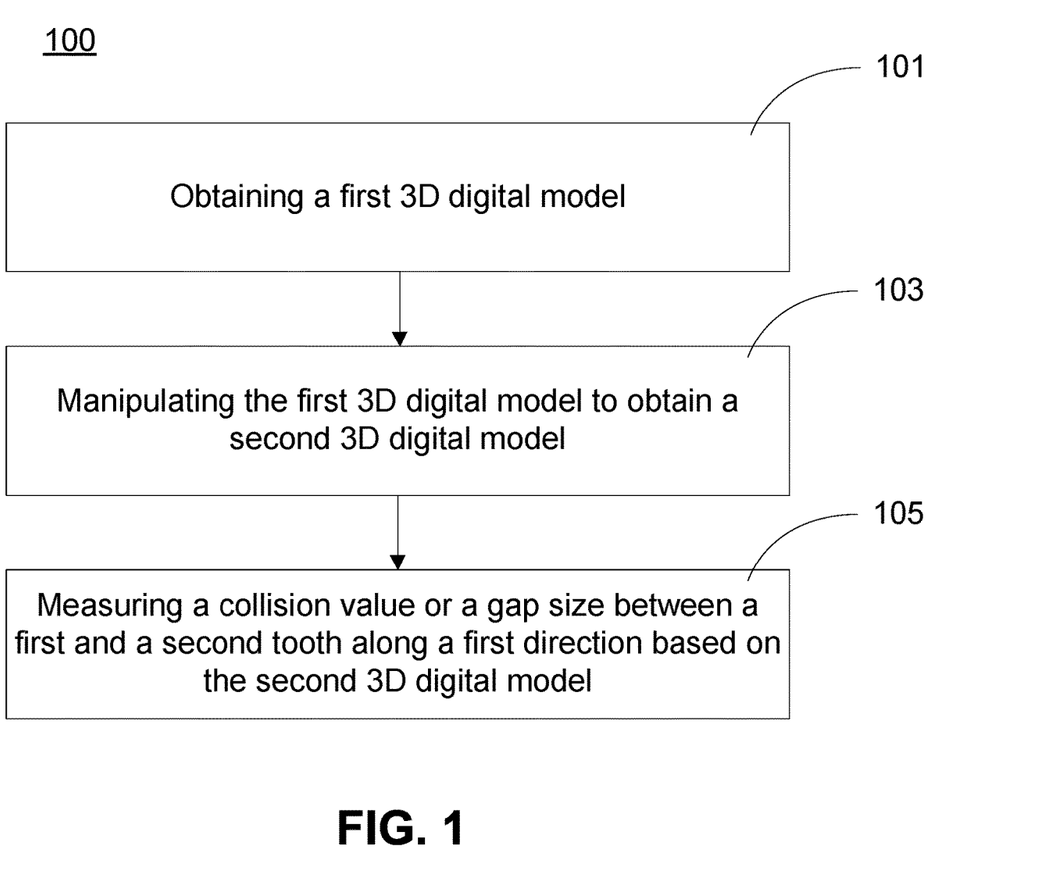
FIG. 1 illustrates a schematic flow chart of a method of measuring relative positional relationship of teeth according to one embodiment of the present application.

Referring to FIG. 1, it illustrates a schematic flow chart of a method 100 of measuring relative positional relationship of teeth according to one embodiment of the present application.

In 101, a first 3D digital model representing a plurality of teeth under a first tooth arrangement is obtained, where the plurality of teeth at least comprise a first tooth and a second tooth.

It is understood that the first 3D digital model may be a 3D digital model representing a whole dentition, or a 3D digital model representing partial dentition.

In one embodiment, the first tooth arrangement is different from a target tooth arrangement of orthodontic treatment. For example, the first tooth arrangement may be a tooth arrangement before the orthodontic treatment is performed or a tooth arrangement during the orthodontic treatment.

There are many methods of obtaining 3D digital models of a patient's teeth. In one embodiment, the 3D digital model of the patient's current tooth arrangement may be obtained by directly scanning the patient's jaw (upper jaw or lower jaw). In another embodiment, a 3D digital model representing the patient's original tooth arrangement may be obtained by scanning a mockup model, e.g., a plaster model of the patient's jaw. In a further embodiment, a 3D digital model representing the patient's current tooth arrangement may be obtained by scanning an impression of the patient's jaw.

In 103, the first 3D digital model is manipulated to obtain a second 3D digital model which represents the plurality of teeth under a second tooth arrangement.

In one embodiment, if only positional relationship between a first tooth and a second tooth needs to be measured, then under the second tooth arrangement, the first tooth and the second tooth may be at their target positions of orthodontic treatment, and other teeth (if any) may be at their target positions of orthodontic treatment or not.

Inspired by the present application, it is understood that if the first and the second tooth do not need orthodontic treatment, or the relative positional relationship between them under the current tooth arrangement is sufficiently close to the relative positional relationship when the first and the second tooth are at their target positions of orthodontic treatment, the relative positional relationship between the first and the second tooth may be directly measured based on the first 3D digital model.

In one embodiment, the first 3D digital model may be graphically presented through a human-machine interaction interface of a computer; a dental professional may input instructions of repositioning the first and/or the second tooth based on the presented images and experience; the computer may modify the first 3D digital model according to the received user instructions, to obtain the second 3D digital model.

Inspired by the present application, it is understood that method of manipulating the first 3D digital model to obtain the second 3D digital model is not limited to the above. In a further embodiment, a specific computer method can be used to automatically manipulate the first 3D digital model.

In 105, a collision value or a gap size between the first and the second tooth is measured along a predetermined first direction based on the second 3D digital model.

A collision value or a gap size can be measured along the predetermined first direction according to specific cases and needs so as to make it more valuable to clinical medicine.

In one embodiment, the first direction may be obtained by calculation. In another embodiment, the first direction may also be designated by a dental professional according to specific cases and needs, for example, through a human-machine interaction interface of a computer.

Figure 2:
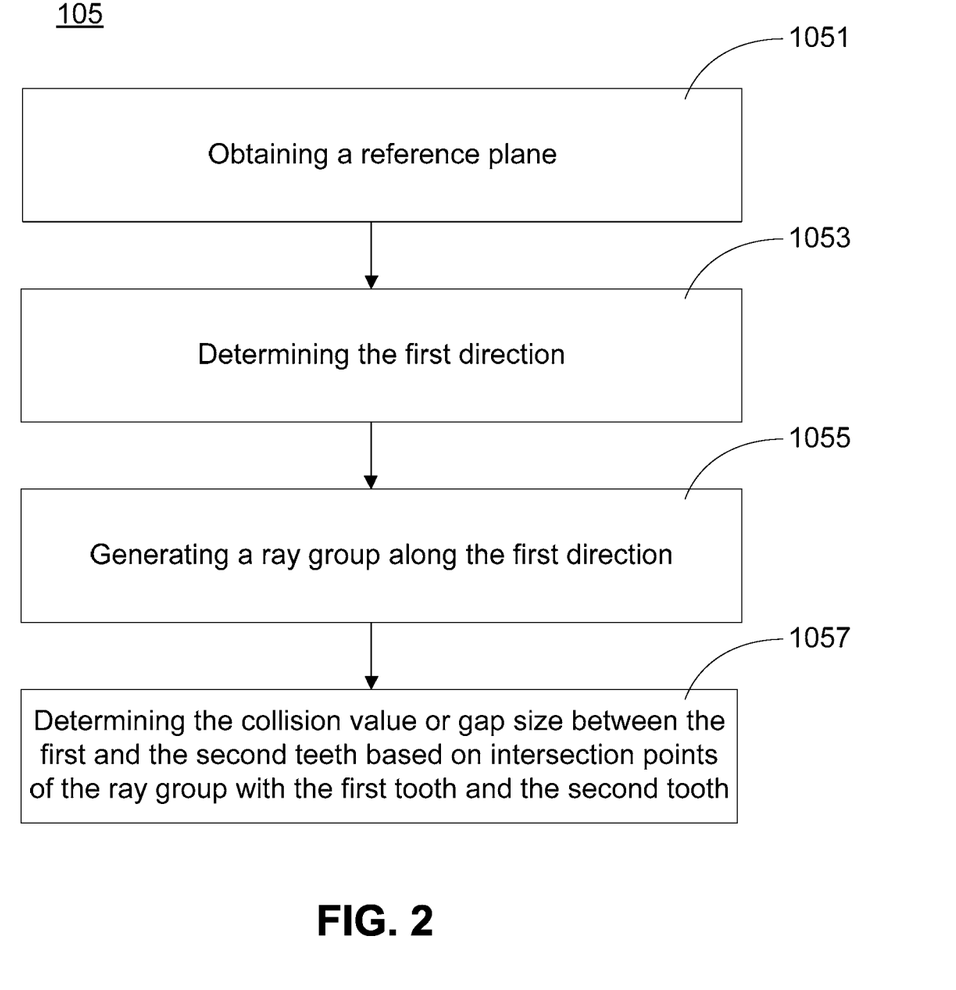
FIG. 2 illustrates a schematic flow chart of 105 shown in FIG. 1 according to one embodiment of the present application.

Referring is made to FIG. 2 which illustrates a schematic flow chart of 105 according to one embodiment of the present application.

In 1051, a reference plane is obtained.

In one embodiment, the reference plane may be a functional occlusal plane. In one embodiment, the second 3D digital model may represent an entire dentition under a target tooth arrangement, and the reference occlusal plane may be calculated based on the second 3D digital model. In another embodiment, the first 3D digital model may represent an entire dentition under the current tooth arrangement, and the reference occlusal plane may also be calculated based on the first 3D digital model.

The functional occlusal plane may also be referred to as a natural occlusal plane which is an imaginary reference plane. In one embodiment, it may be obtained basis the mean of the Z coordinates of occlusal contact points of posterior teeth.

Figure 3:
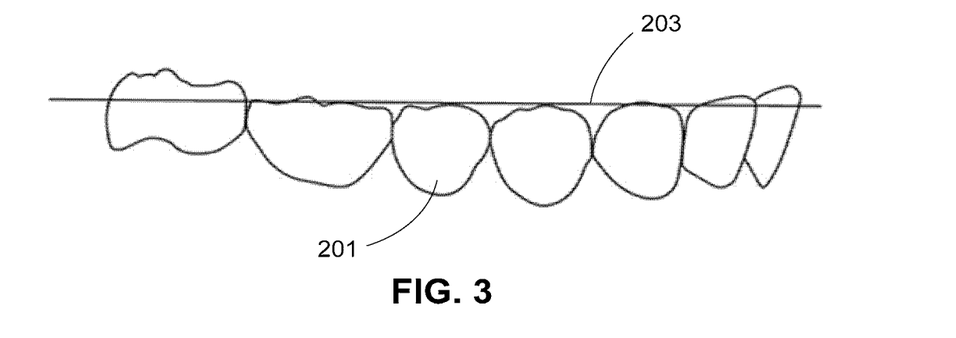
FIG. 3 schematically illustrates positional relationship between a jaw and a functional occlusal plane according to one embodiment of the present application.

Referring is now made to FIG. 3, which schematically illustrates positional relationship between a 3D digital model of teeth 201 and its functional occlusal plane 203 in one embodiment of the present application.

In one embodiment, a total of six teeth from a first premolar to a first molar may be selected as key teeth, and feature points of the key teeth may be taken as key points (only one feature point may be selected on each tooth). Then reasonable key points may be selected from the key points, and a plane can be obtained through fitting using the reasonable key points to be taken as the functional occlusal plane.

If there are seriously mal-positioned teeth, the key teeth need to be screened, and key points deviating much along a vertical direction may be screened out. Take first premolar as an example. If there are first premolars on both left and right sides, and a height difference of the two premolars is greater than 3 mm, it indicates that the position of one of the first premolars is abnormal. A difference with average heights of the key teeth on the same side may be calculated for each of the first premolars, and the first premolar having a larger difference may be screened out.

In one embodiment, if the jaw, on which the teeth to be measured are located, does not have sufficient key teeth to determine the function occlusal plane, a total of six teeth from a first premolar to a first molar on the opposite jaw may be selected as key teeth, to determine the function occlusal plane.

In another embodiment, if there are just three key teeth, a plane determined by three key points on the three key teeth may be taken as the functional occlusal plane.

In a further embodiment, if the number of key teeth is less than three, and the number of corresponding key points is also less than three, it is not possible to fit a plane using the key points, and a horizontal plane may be taken as the reference plane.

In 1053, the first direction is determined.

It should be noted that in one embodiment, to simplify calculation, in a 3D digital model representing a dentition, position and pose of each tooth may be determined based on a global coordinate system and a local coordinate system of the tooth. In one embodiment, the x-axis of a local coordinate system of a tooth may be in a mesiodistal direction of the tooth, and the z-axis may be in a vertical direction. Inspired by the present application, it is understood that establishment of a local coordinate system is not limited to the example. For example, the method of establishing a local coordinate system disclosed in the Chinese patent application No. 201611244728.4 entitled "Computer-Aided Method of Simplifying Orthodontic Treatment Path" filed on Dec. 29, 2016 by the Applicant of the present application, may also be used.

Figure 4:
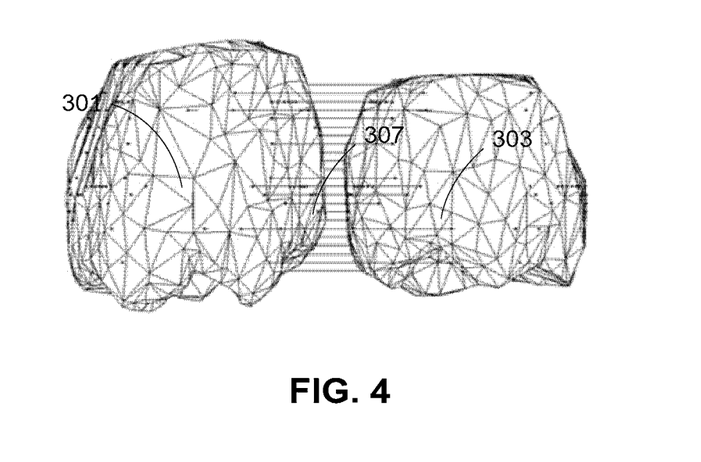
FIG. 4 schematically illustrates 3D models of a first tooth and a second tooth and a generated ray group according to one embodiment of the present application.

Referring to FIG. 4, it schematically illustrates 3D models of a first tooth 301 and a second tooth 303 to be measured in one embodiment of the present application.

In one embodiment, a first direction $v_{xm}$ (namely, a collision or gap direction) may be determined by the following method.

The x-axis of a local coordinate system of the first tooth 301 is projected on the functional occlusal plane and then normalized to obtain a direction vector $v_{x1}$. The x-axis of a local coordinate system of the second tooth 303 is projected on the functional occlusal plane and then normalized to obtain a direction vector $v_{x3}$. If an angle between directions of $v_{x1}$ and $v_{x3}$ is greater than 90 degrees, $v_{x3}$ may be reversed. Then, an average vector of $v_{x1}$ and $v_{x3}$ is normalized to obtain a direction vector $v_{xm}$.

A ray may be generated from a point that is infinitely far along this direction. If the ray intersects with both the first tooth 301 and second tooth 303, the positional relationship between the first tooth 301 and second tooth 303 may be deduced based on the positional relationship between intersection points.

Inspired by the present application, it is understood that determination of the first direction is not limited to the above method. For example, a line that goes through the origins of the local coordinate systems of the first tooth 301 and second tooth 303 may also be taken as the first direction. The direction of a tangent at a midpoint between the first tooth 301 and second tooth 303 on the dental arch curve may also be taken as the first direction. The first direction may be determined according to specific cases and needs.

In 1055, a ray group is generated along the first direction.

To improve calculation efficiency, the first tooth 301 and second tooth 303 may be projected on a first plane perpendicular to the first direction, and a ray group may be generated within an overlap area of the projections of the first tooth 301 and the second tooth 303.

Figure 5:
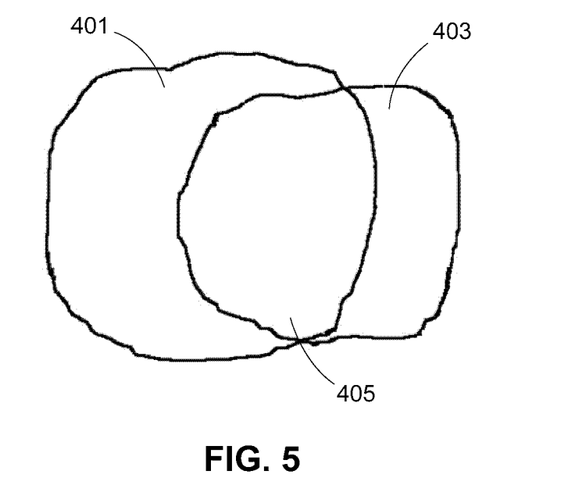
FIG. 5 schematically illustrates projection of the first and the second tooth shown in FIG. 4 on a plane perpendicular to a first direction.

Referring to FIG. 5, it schematically illustrates a projection 401 of the first tooth 301 on the first plane, a projection 403 of the second tooth 303 on the first plane, and an overlap area 405 of the two projections.

In one embodiment, sampling may be performed within the overlap area 405 using a fixed step to obtain a set of sampling points, and then a ray group, which are along the first direction and go through these sampling points, are generated. It is understood that the smaller the step, the higher the precision, and the more calculation complexity. The sampling step may be determined according to specific situations and needs. For example, the sampling step may be 0.05 mm.

In another embodiment, the sampling step may be variable, e.g., may vary with curvature, e.g., the larger the curvature, the higher the sampling density. Inspired by the present application, it is understood that the sampling method is not limited to the above, and any suitable sampling method may be used, which will not be described in detail here.

In a further embodiment, to simplify calculation, a minimum first rectangle on the first plane may be generated based on a maximum value and a minimum value of coordinates of the projection of the first tooth 301 on the first plane, and a minimum second rectangle on the first plane may be generated based on a maximum value and a minimum value of coordinates of the projection of the second tooth 303 on the first plane, and then sampling may be carried out within an overlap area of the first rectangle and second rectangle.

In 1057, the collision value or the gap size between the first tooth and the second tooth is determined based on the intersection points of the ray group and the first and the second tooth.

In one embodiment, for each ray in the ray group, its intersection points with the first tooth 301 and the second tooth 303 may be calculated. Since each of the 3D digital models of the first tooth 301 and the second tooth 303 form a closed surface, if the number of intersection points of a ray with one of the teeth is less than two, the ray may be regarded as an invalid ray. Referring to FIG. 4, it schematically illustrates a generated ray group 307 according to one embodiment of the present application.

It is assumed that there are two intersection points $A_1$ and $A_2$ between a ray and the first tooth, and there are four intersection points $B_1$, $B_2$, $B_3$ and $B_4$ between the ray and the second tooth. A vector $A_iB_j$ from any $A_i$ ($1 \leq i \leq 2$) to any $B_j$ ($1 \leq j \leq 4$) may be established. The length of each vector may be calculated and stored in vector sets $\{A_iB_j | x \geq 0\}$ and $\{A_iB_j | x < 0\}$ according to the direction of the vector.

If one of the vector sets $\{A_iB_j | x \geq 0\}$ and $\{A_iB_j | x < 0\}$ is empty, meaning that all vectors are in the same direction, the intersection points of the first tooth and second tooth with the ray are respectively located on two sides, then there is a gap between the first tooth and second tooth at this sampling point in the first direction, and the size of the gap equals the minimum vector length.

Figure 6A:
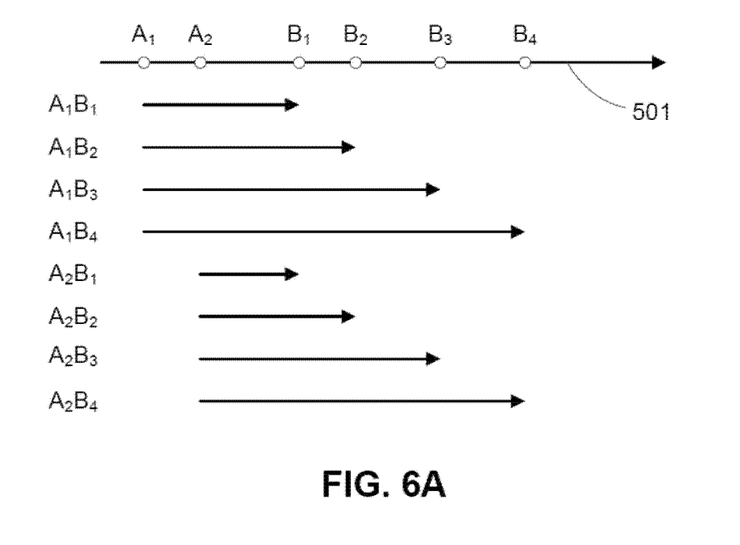
FIG. 6A schematically illustrates rays and a corresponding vector set according to one embodiment of the present application.

Referring to FIG. 6A, which schematically illustrates a vector set in a case that there is a gap between the first tooth and the second tooth at a sampling point and in the first direction according to one embodiment of the present application.

A ray 501 has intersection points $A_1$ and $A_2$ with the first tooth, and has four intersection points $B_1$, $B_2$, $B_3$ and $B_4$ with the second tooth, where the length of the vector $A_2B_1$ is the gap size between the first tooth and second tooth at the sampling point along the first direction.

If both vector sets have vectors, there are intersection points on the first tooth and second tooth which are closer to the other tooth's side than at least one intersection point on the other tooth, and there is collision between the first tooth and the second tooth at the sampling point.

Figure 6B:
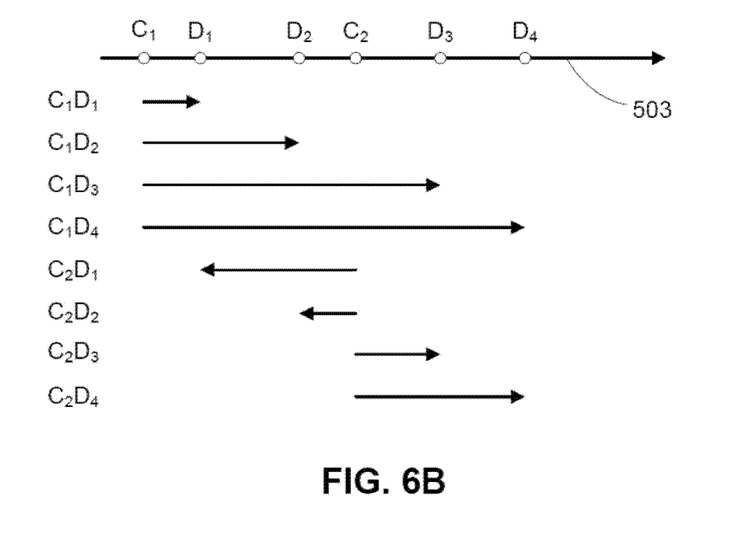
FIG. 6B schematically illustrates rays and a corresponding vector set according to another embodiment of the present application.

Referring to FIG. 6B, it schematically illustrates a vector set in a case that there is collision between the first tooth and the second tooth at a sampling point along the first direction according to one embodiment of the present application.

In this example, a ray 503 has intersection points $C_1$ and $C_2$ with the first tooth, and has four intersection points $D_1$, $D_2$, $D_3$ and $D_4$ with the second tooth, where the length of the vector $C_2D_1$ is the value of the collision between the first tooth and the second tooth at the sampling point along the first direction.

In this case, the direction of the vector with the longest modulus in the two vector sets represents the direction in which the two teeth are arranged, namely, vector $C_1D_4$, whereas a vector in a direction opposite thereto represents the collision between the two teeth, namely, vector $C_2D_1$ and $C_2D_2$, where the length of the vector $C_2D_1$ with a longer modulus is the collision value between the two teeth.

It is understood that one ray corresponds to a group of vector sets, and the positional relationship between two teeth at the corresponding sampling point along the first direction may be determined based on the group of vector sets. The positional relationship between the two teeth can be determined by traversing the positional relationships between the two teeth at all sampling points along the first direction. For example, if there is collision between the two teeth at at least one sampling point, the maximum collision value may be identified among the collision values at these sampling points and taken as the collision value between the two teeth. If there is no collision between the two teeth at any sampling points, the minimum gap size may be identified among the gap sizes at these sampling points and taken as the gap between the two teeth.

Inspired by the present application, it is understood that many parts of the method of measuring the positional relationship between two teeth according to the present application may be automatically performed by the computer, particularly those parts involving large amounts of calculation, for example, sampling points, generating rays, generating vector sets, determining positional relationship between two teeth based on vector sets etc.

Another aspect of the present application provides a computer system for measuring the positional relationship between two teeth, and the computer system comprises a computing device and an input/output device connected thereto. In one embodiment, the input/output device may comprise an input device such as a keyboard and/or mouse, and an output device such as a display and/or a printer. The computing device may comprise a processor and a storage device, the storage device is connected to the processor and stores therein computer instructions, which will cause the computing device to execute the method of measuring positional relationship between two teeth according to the present application when they are executed by the processor.

While various aspects and embodiments have been disclosed herein, other aspects and embodiments will be apparent to those skilled in the art. The various aspects and embodiments disclosed herein are for illustration only and are not intended to be limiting, and the scope and spirit of the present application shall be defined by the following claims.

Likewise, the various diagrams may depict exemplary architectures or other configurations of the disclosed methods and systems, which are helpful for understanding the features and functions that can be included in the disclosed methods and systems. The claimed invention is not restricted to the illustrated exemplary architectures or configurations, and desired features can be achieved using a variety of alternative architectures and configurations. Additionally, with regard to flow diagrams, functional descriptions and method claims, the order in which the blocks are presented herein shall not mandate that various embodiments of the functions shall be implemented in the same order unless otherwise the context specifies.

Unless otherwise specifically specified, terms used herein are generally intended as "open" terms instead of limiting. In some embodiments, use of phrases such as "one or more", "at least" and "but not limited to" should not be construed to imply that the parts of the present application that do not use similar phrases intend to be limiting.

We claim:

1. A computer-based method of measuring positional relationship between two teeth, comprising:
   obtaining a second 3D digital model representing a plurality of teeth under a second tooth arrangement, wherein the plurality of teeth comprise a first tooth and a second tooth;
   measuring a collision value or a gap size between the first tooth and second tooth based on the second 3D digital model and a predetermined first direction;
   generating a ray group along the first direction;
   determining the collision value or the gap size between the first tooth and the second tooth based on intersection points of the ray group and the first and the second tooth;
   projecting the first tooth and the second tooth on a first plane perpendicular to the first direction; and
   sampling in an overlap area of projections of the first tooth and the second tooth to obtain a sampling point set, wherein the ray group is generated based on the sampling point set.

2. The method of claim 1, wherein the first tooth and second tooth are at their target positions of orthodontic treatment under the second tooth arrangement.

3. The method of claim 2, further comprising determining the first direction based on a second direction and a third direction, wherein the second direction is a mesiodistal direction of the first tooth and the third direction is a mesiodistal direction of the second tooth when the first and the second tooth are under the second tooth arrangement.

4. The method of claim 3 further comprising:
   selecting a reference plane;
   projecting unit vectors representing the second direction and the third direction respectively on the reference plane, to obtain a first unit vector and a second unit vector; and
   calculating an average vector of the first unit vector and the second unit vector, wherein the direction of the average vector is taken as the first direction.

5. The method of claim 4, wherein the reference plane is a functional occlusal plane.

6. The method of claim 4, wherein the reference plane is a horizontal plane.

7. The method of claim 2 further comprising:
   obtaining a first 3D digital model representing the plurality of teeth under a first tooth arrangement which is different from the second tooth arrangement; and
   manipulating the first 3D digital model to obtain the second 3D digital model.

8. The method of claim 1 further comprising:
   generating a vector set for each ray in the ray group using intersection points of the ray with the first tooth and the second tooth; and
   determining the collision value or the gap size between the first tooth and second tooth based on the vector sets.

* * * * *